(12) United States Patent
Akerfeldt

(10) Patent No.: US 10,959,709 B2
(45) Date of Patent: Mar. 30, 2021

(54) BIOPSY DEVICE

(71) Applicant: APRIOMED AB, Uppsala (SE)

(72) Inventor: Dan Akerfeldt, Knivsta (SE)

(73) Assignee: APRIOMED AB, Uppsala (SE)

( * ) Notice: Subject to any disclaimer, the term of this patent is extended or adjusted under 35 U.S.C. 154(b) by 819 days.

(21) Appl. No.: 15/028,563

(22) PCT Filed: Oct. 9, 2014

(86) PCT No.: PCT/EP2014/071610
§ 371 (c)(1),
(2) Date: Apr. 11, 2016

(87) PCT Pub. No.: WO2015/055490
PCT Pub. Date: Apr. 23, 2015

(65) Prior Publication Data
US 2016/0249890 A1 Sep. 1, 2016

(30) Foreign Application Priority Data
Oct. 16, 2013 (EP) .................................... 13188849

(51) Int. Cl.
*A61B 5/00* (2006.01)
*A61B 10/02* (2006.01)
(52) U.S. Cl.
CPC ...... *A61B 10/0266* (2013.01); *A61B 10/0275* (2013.01); *A61B 2010/0208* (2013.01)
(58) Field of Classification Search
CPC . A61B 10/02; A61B 10/0208; A61B 10/0233; A61B 10/0266–0275; A61B 17/8819; A61B 17/8825; A61B 10/27

USPC .......................................................... 600/562
See application file for complete search history.

(56) References Cited

U.S. PATENT DOCUMENTS

| 3,477,423 A | 11/1969 | Griffith |
| 4,907,599 A * | 3/1990 | Taylor ................ A61B 10/0275 600/567 |
| 4,958,625 A * | 9/1990 | Bates ................ A61B 10/0275 600/562 |
| 5,423,824 A | 6/1995 | Akerfeldt et al. |

(Continued)

FOREIGN PATENT DOCUMENTS

| WO | WO-93/20753 A1 | 10/1993 | |
| WO | WO 9320753 A1 * | 10/1993 | ......... A61B 10/0275 |

*Primary Examiner* — Max F Hindenburg
(74) *Attorney, Agent, or Firm* — Foley & Lardner LLP

(57) ABSTRACT

The present invention relates to a biopsy assembly for obtaining a tissue sample, comprising an outer tubular cannula provided with an oblique distal tip, and a stylet adapted to be disposed axially within said cannula and having an oblique distal tip. The stylet is provided with a recess arranged along a side of the stylet which is adapted to receive the tissue sample. The assembly further comprises a housing for guiding and manipulating the proximal ends of the cannula and the stylet and is provided with a rotating member configured to rotate the stylet or cannula around a common axis, such that the cannula and the stylet are rotated relative to one another. The rotating member is configured to rotate the stylet and cannula relative to one another prior to tissue sampling, such that a most distal edge of the oblique distal tip of said cannula is arranged at the same side as the recess when the tissue sampling is performed.

8 Claims, 5 Drawing Sheets

(56) References Cited

U.S. PATENT DOCUMENTS

| | | | |
|---|---|---|---|
| 5,425,376 A * | 6/1995 | Banys | A61B 10/0275 600/566 |
| 5,487,392 A | 1/1996 | Haaga | |
| 5,810,826 A | 9/1998 | Akerfeldt et al. | |
| 6,273,861 B1 | 8/2001 | Bates et al. | |
| 2010/0298737 A1 | 11/2010 | Koehler | |
| 2011/0190660 A1 * | 8/2011 | Levy | A61B 10/0275 600/566 |
| 2012/0172752 A1 * | 7/2012 | Ranpura | A61B 10/0275 600/567 |

* cited by examiner

BIOPSY DEVICE

FIELD OF THE INVENTION

The present invention relates to a biopsy device, and in particular to an improved biopsy device for obtaining a tissue sample, according to the preamble of the independent claim.

BACKGROUND OF THE INVENTION

Biopsy sampling is often performed with biopsy devices comprising a stylet with a recess for sample capturing placed on one side of the stylet, close to the distal end. The stylet is contained within a cannula, which functions both to cut the sample and to shield it for later retrieval, after removal of the device from a patient.

One such device is shown in U.S. Pat. No. 3,477,423 describing a biopsy device comprising a needle with a side pocket for obtaining a tissue sample and a cutting outer sheath. Another similar device is shown in U.S. Pat. No. 5,487,392, which, in addition to a stylet with a side pocket for tissue sampling and a cutting cannula, further comprises a hemostatic insert to minimize bleeding after sampling. A further biopsy assembly is describe in U.S. Pat. No. 6,273,861, wherein a stylet and cutting cannula together with an insertion device is mounted in an insertion assembly utilizing pneumatic activation for impelling the excising means. U.S. Pat. No. 5,425,376 shows another biopsy device, wherein a cannula is mounted over a hollow needle, and provided with a hub that may be rotated relative the needle. US Patent Application 2010/0298737 describes another type of cutting device, comprising a curved distal portion of a stylet arranged within a cannula, wherein the curvature can be varied by a rotational movement of the cannula relative to the stylet.

Biopsy sampling can be performed in different types of tissue. When sampling in e.g. bone tissue or sclerotic lesions, biopsy sampling may be difficult to carry out with the aid of a traditional biopsy needle, as in bone the lesion is often delimited by the hard surface layer of the bone, namely the cortical bone tissue. Today there are several known methods to gain access to a lesion in the bone, and one way is to introduce a drill equipped with a cannula, drill through the cortical bone, and then remove the drill. Thereafter, a biopsy needle may be introduced through the cannula to obtain a biopsy sample. One such example is described in U.S. Pat. Nos. 5,810,826 and 5,423,824, which are assigned to the present assignee, and are hereby incorporated by reference for the devices and methods described therein.

Traditional biopsy devices are inserted percutaneously with the stylet contained within the cannula and positioned next to or in the sample site. To ensure a smooth entry, both the cannula and stylet are provided with obliquely angled and sharpened tips. By moving the stylet in a distal direction and/or the cannula in a proximal direction, the sample recess is exposed to the tissue of interest, which is pressed into the sample recess. By thereafter moving the cannula distally the leading edge of the cannula will cut the sample tissue and the cannula wall will contain it within the recess. This arrangement necessitates a relatively long part of the stylet distal to the sample recess, due to the distance needed for the slanted tip distal of the cutting edge of the cannula, and the need to ensure that the sample is fully contained within the recess and cannula. However, this leads to a problem when a desired tissue sample site is close to hard structures, such as bone tissue, as a sample cannot be obtained closer than the distal tip distance. Also, a long distance between the sharp distal tip and the sample recess presents a risk when a desired tissue sample site is close to sensitive tissue, such as tissue more prone to bleeding, or tissue that for other reasons is preferably not cut or penetrated.

The inventor of the present invention has therefore identified a need for an improved biopsy device.

An object of the present invention is to provide a biopsy device which allows tissue sampling closer to structures or tissue that cannot and/or should not be penetrated during a biopsy procedure.

SUMMARY OF THE INVENTION

The above-mentioned objects are achieved by the present invention according to the independent claims.

Preferred embodiments are set forth in the dependent claims.

Thus, a biopsy assembly is provided for obtaining a tissue sample that comprises an outer tubular cannula provided with an oblique distal tip, and a stylet adapted to be disposed axially within said cannula and being provided with an oblique distal tip. The stylet has a recess arranged along one side adapted to receive the tissue sample. The biopsy assembly further comprises a housing for guiding and manipulating the cannula and stylet, and a rotating member mounted at a proximal end of the stylet or the cannula and configured to rotate the stylet or the cannula around a common axis, such that the cannula and the stylet are rotated relative to one another prior to tissue sampling. Thereby the distal edge of the oblique distal tip of the cannula is arranged at the same side as the recess when the tissue sampling is performed, and optimal severing of the tissue sample is achieved.

By providing a biopsy assembly wherein the stylet and cannula are configured to be rotated in relation to each other prior to sampling, a sample can be taken closer to the distal tip of the assembly, as the recess is arranged closer to the tip without compromising the reliability of sample acquisition.

SHORT DESCRIPTION OF THE APPENDED DRAWINGS

DETAILED DESCRIPTION OF PREFERRED EMBODIMENTS OF THE INVENTION

In the following, the terms "distal" and "forward" refer to a direction towards a tissue site in a patient's body, away from a user of a biopsy assembly. Hence, the terms "proximal" and "back" refer to a direction away from the tissue sample site, and closer to a user.

Figure 1A:
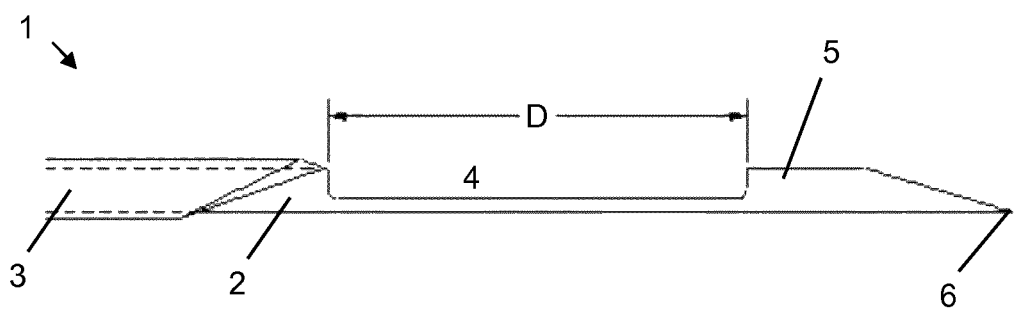
FIGS. 1a and 1b illustrates a distal part of a biopsy assembly according to prior art.

FIG. 1a show a distal part of a biopsy assembly 1 according to prior art. A solid stylet or needle 2 is arranged within a cannula 3. The stylet 2 is provided with a recess 4 along one side of the stylet having a longitudinal distance D.

This distance can be adapted to suit individual sampling needs, depending on the tissue type and size of desired tissue in a patient's body. During tissue sampling the recess is exposed to the surrounding tissue, as is illustrated in FIG. 1a. Hence, a longer distance D corresponds to a larger tissue sample, but also necessitates both a larger sample site, such that a homogenous tissue sample can be obtained, and that the stylet is axially displaced in relation to the cannula to a larger extent during tissue sampling.

Figure 1B:
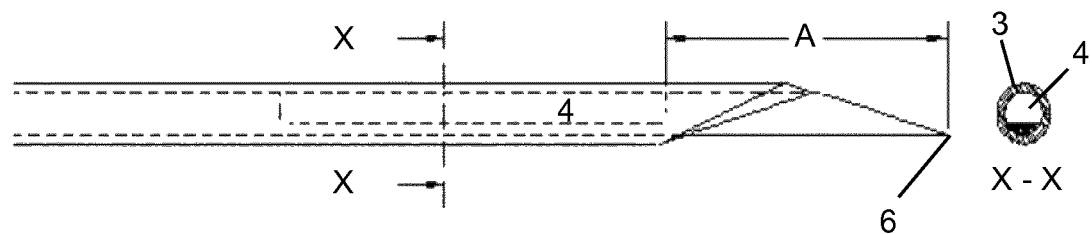

As illustrated in FIG. 1b, during insertion through the skin and other tissue of a patient the prior art stylet tip normally protrudes slightly from the cannula, to ensure smooth entry and that no tissue or other matter, such as body fluid, enters the recess prematurely, which could result in a tissue sample comprising non-desired tissue. A cross-section X-X shows that when the stylet is retracted into the cannula, the recess 4 is enclosed by the cannula walls 3, to completely retain the sample for safe removal of the assembly from the sample site and from the patient's body before retrieving the sample for any desired purpose. The drawback of the prior art assembly is that a relatively long solid stylet tip 5 is needed, defined by length A, i.e. the distance from the distal end of the recess 4 to the extreme distal end 6 of the stylet tip 5. The length A must be at least a length such that it is ensured that no undesired tissue or fluid can enter the recess during insertion or retraction. Therefore the distal end of the recess 4 must be a certain length from the proximal edge of the oblique tip of the cannula 3, such that the recess is covered by the cannula when the stylet tip is slightly protruding from the cannula (as shown in FIG. 1b). The length A of solid stylet tip 5 also determines the minimum distance between a desired sample tissue, to be retained in recess 4, and other tissue that is either hard to penetrate or undesirable to penetrate with the stylet tip 6. Non-limiting examples of hard tissue are bone or cartilage. Non-limiting examples of tissue which is undesirable to penetrate is tissue which is hypersensitive to leakage or bleeding, tissue where penetration is especially painful to the patient, tissue that could contaminate the desired sample, or tissue which for other reasons it is especially important not to penetrate or cut.

As an example, if a desired tissue sample site is located adjacent to a bone structure, the sample can, at best, only be taken at a minimum distance from the bone tissue defined by length A, as the tip 6 of the stylet cannot, for any practical purposes, penetrate bone. Furthermore, if a tissue mass is small in size, the length A of the solid stylet tip 5 could impair or even prevent taking a sample of the desired tissue. Therefore, one objective of the present invention is to provide a biopsy assembly wherein the necessary distance during use between the extreme distal tip of the assembly and the sample recess is considerably shortened, without adding any risk of failure or damage to the patient.

It is to be noted that in the prior art device illustrated in FIG. 1, the leading edge of the cannula must be located on the same side as the recess, to ensure a clean cut when severing the tissue.

Figure 2:
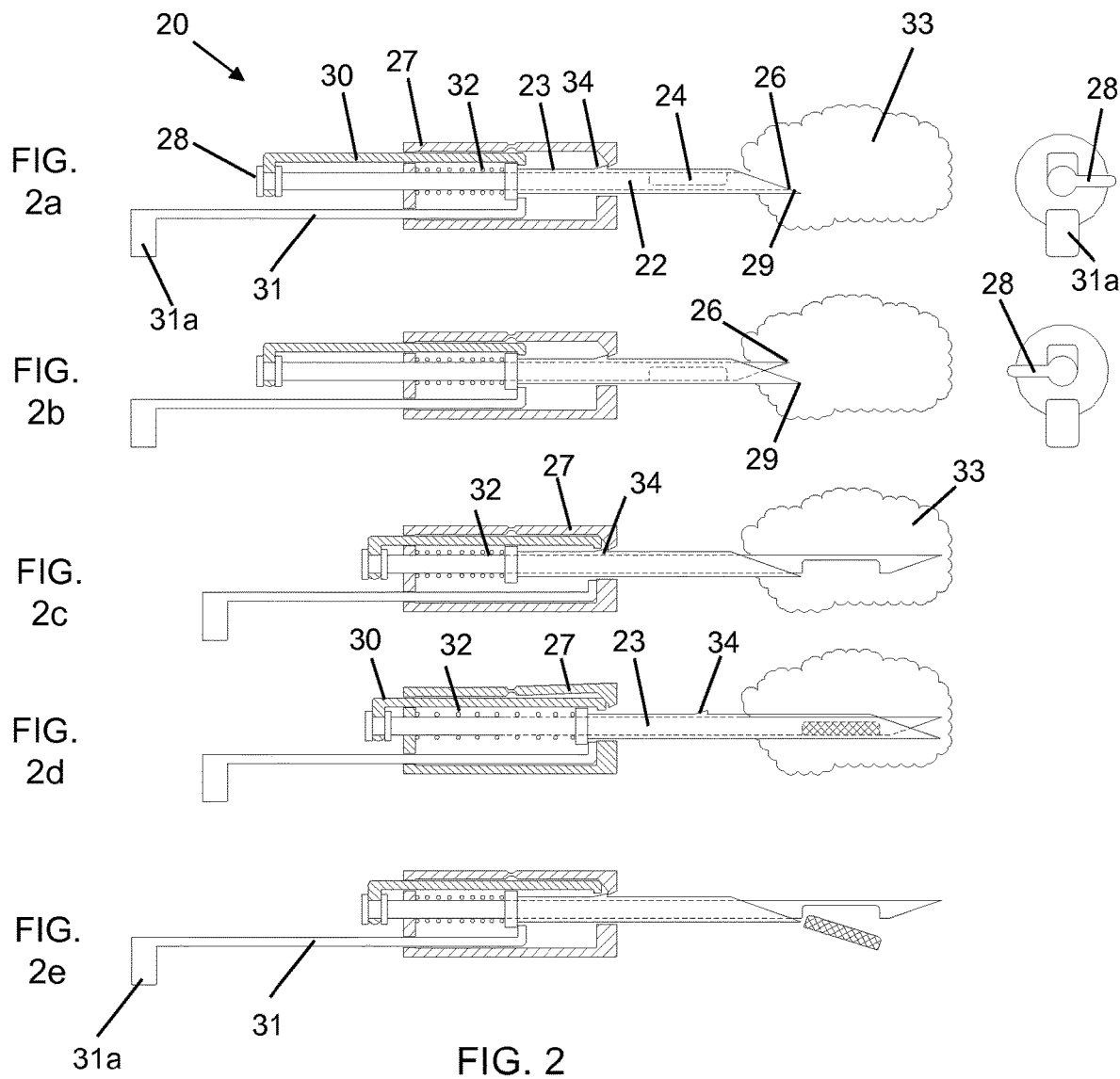
FIG. 2 illustrates a distal part of a biopsy assembly according to the present invention.

FIG. 2 illustrates a first embodiment of the present invention and its function. The figures are side views of an assembly in different stages of operation, where the proximal end is on the left side and the distal end is on the right side of the figure. A stylet or needle 22 is arranged within a cannula 23. Both the stylet 22 and the cannula 23 are provided with oblique tips, essentially slanted at equivalent angles, such that the leading edge of the assembly initially forms an essentially integrated slanted surface with a sharp tip, the tip comprising the stylet tip 26 in alignment with the cannula tip 29, as illustrated in FIG. 2a. Parts of the stylet 22 and the cannula 23 are arranged within a housing 27 for guiding and manipulating the operation of the stylet 22 and the cannula 23. The proximal end of the stylet 22 is fixedly attached to an elongated retaining member 30, which at its distal end is arranged to retain the cannula 23 by holding on to a proximal ledge of the cannula 23. The proximal end of the cannula 23 is held in place by, on one hand, the retaining member 30 preventing the cannula 23 from moving in a distal direction, and, on the other hand, a compression spring 32 arranged between the proximal end of the cannula 23 and a proximal part of the housing 27 preventing the cannula from moving in a proximal direction. The cannula 23 is furthermore prevented from moving distally within the housing 27 by a retaining protrusion 34 on the cannula 23, which abuts a distal end of the housing 27. The stylet 22 and cannula 23 are thereby held in longitudinal alignment by the cooperation of the retaining member 30, the spring 32, and the retaining protrusion 34.

In this embodiment, an elongated retraction member 31 is also initially arranged in cooperation with a proximal ledge of the cannula 23. At its proximal end, the retraction member 31 is provided with a handle or knob 31a which protrudes proximally out of the housing 27. However, unlike the retaining member 30, the retraction member 31 is not fixedly attached to either the stylet 22, the cannula 23 or the housing 27. The function of the retraction member 31 will be described below.

In use, the biopsy assembly 20 is inserted percutaneously into a patient's body, such that the distal end is placed adjacent or slightly inserted into a tissue mass 33 from which a sample is desired. For simplicity, the skin and other tissue is not shown in the figures. In one embodiment the assembly can be inserted on its own, through e.g. soft tissue. In another embodiment, if a sample site is located behind or within a hard tissue, such as bone or cartilage, a drill arrangement can be used to create an access hole for the assembly. Such drills and other access devices are well known in the art. One example is described in U.S. Pat. Nos. 5,810,826 and 5,423,824, which are assigned to the present assignee, and are hereby incorporated by reference for the devices and methods described therein.

The stylet 22 is provided with a recess 24 along one side of the solid stylet 22. The recess 24 is arranged on the same side as the proximal edge of the slanted tip, as can be seen in the side views of FIG. 2. After insertion of the biopsy assembly 20, the stylet 22 and cannula 23 are rotated in relation to each other, such that the recess 24 is moved from one side to the opposite side in relation to the cannula 23.

In the embodiment of FIG. 2, a rotating member 28 is arranged in operative connection with the proximal end of the stylet 22, configured such that when the rotating member 28, e.g. in the form of a handle or knob, is rotated, the stylet 22 will rotate within the cannula 23, such that the recess 24 is moved from one side to the opposite side in relation to the cannula 23. This is illustrated in the difference between FIGS. 2a and 2b. The drawings on the far right show a proximal view of the biopsy assembly depicted in the respective left drawing. As can be seen when comparing the configuration of the assembly in FIG. 2a with that of FIG. 2b, when the handle of rotating member 28 is rotated approximately 180 degrees, the stylet 22 is rotated within the cannula 23.

However, as an alternative (not shown in the figures) a rotating member can be configured to rotate the cannula 23 instead, keeping the stylet 22 and housing 27 rotationally fixed in relation to each other.

In yet another embodiment, the rotation of the stylet 22 or cannula 23 can be automatic, by mounting a torsion spring within or outside the housing 27, such that a user can release the spring force by e.g. pressing a button, whereby that the stylet 22 or cannula 23 is rotated 180 degrees by the torsion spring, resulting in the configuration of FIG. 2b. In this embodiment, the rotating member is the torsion spring.

Regardless of how the stylet 22 or the cannula 23 is rotated in relation to the rest of the assembly, i.e. whether this movement is executed manually by a user rotating a knob, or automatically by using a torsion spring, the end result regarding the orientation at the distal end of the stylet 22 and the cannula 23 in relation to each other is the same as illustrated in FIG. 2b, i.e. that the stylet 22 and cannula 23 are rotated 180 degrees in relation to each other, and the stylet tip 26 and the cannula tip 29 are on opposite sides of a longitudinal axis of the assembly.

After rotation of the stylet 22 and the cannula 23 in relation to each other, the retaining member 30, which is fixedly attached at its proximal end to the proximal end of the stylet 22 and thereby also to rotating member 28, is pushed by a user in a distal direction, resulting in a configuration as shown in FIG. 2c. Alternatively, the proximal end of the stylet 22 itself or indirectly via the rotating member 28, depending on the configuration of the assembly, is pushed in a distal direction. Regardless of how it is executed, pushing the proximal end of the stylet 22 in a distal direction will cause the stylet 22 to move distally in relation to the housing 27. However, the cannula 23 is still prevented from distal movement by the retaining protrusion 34. Therefore the stylet 22 will protrude out of the cannula 23 such that the sample recess 24 is exposed to the desired tissue 33.

When a user continues to push the stylet 22 in a distal direction, the distal end of the retaining member 30 will slide along the cannula 23 and reach the retaining protrusion 34. The retaining member 30, retaining protrusion 34 and housing 27 are configured such that when the retaining member 30 reaches the distal end of the housing 27, it will press away the housing 27 from the retaining protrusion 34, such that the cannula 23 is released from the retaining protrusion 34. This is illustrated in FIG. 2d. Hereby the cannula 23 is rapidly pushed forward by the action of the spring 32, such that the leading edge of the cannula 23 severs the tissue and retains a tissue sample within the recess 24 and the cannula walls 23.

As an alternative embodiment, not shown the figures, the sampling steps can be fully automatic, such that both the forward movement of the stylet 22 and the subsequent forward movement of the cannula 23 are effected by one or several springs or similar mechanisms, as described for the cannula 23 above. In such an embodiment, a user could initiate the sampling steps by e.g. pressing a button to release stylet 22 from a locked position to freely move forward by the action of e.g. a tension spring, mounted around the proximal end of the stylet 22 between the proximal end and the housing 27. Thereby the stylet 22 is pushed forward into the tissue mass 33, whereby the forward movement of the stylet would, in turn, trigger the release of a compression spring to move the cannula 23 forward.

It is to be noted that in all embodiments of the invention, it is understood that different configurations of spring mechanisms can be used, using one or several compression and/or tension springs, as long as the resulting effect that is achieved is that the recess 24 of the stylet 22 is first exposed to the tissue mass 33, and thereafter the cannula 23 is moved forward to sever the tissue sample.

The embodiments using either semi-automatic or fully automatic sampling steps, as described above, can be combined with either manual or automatic rotation of the stylet 22 and cannula 23 in relation to each other, as described in relation to FIGS. 2a and 2b above.

After the sampling steps have been executed, the biopsy assembly 20 is withdrawn from the sample site and the patient's body, e.g. by pulling on the housing 27 in a proximal direction. When the tissue sample is to be released from the biopsy assembly, the handle or knob 31a of the retraction member 31 is pulled back, such that the cannula 23 is pulled back and the tissue sample is exposed.

Figure 3:
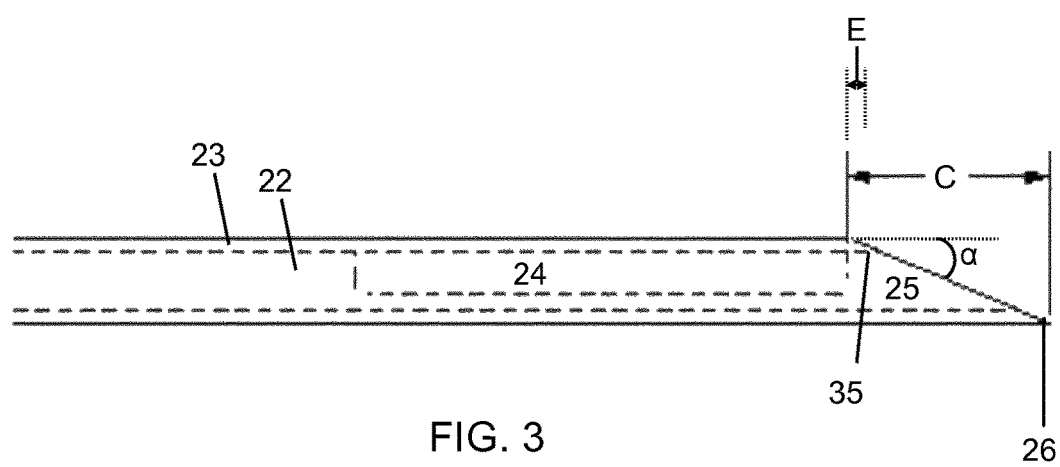
FIG. 3 illustrates one embodiment of a biopsy assembly according to the present invention.

FIG. 3 shows a closer view of a distal part of the biopsy assembly according to the present invention. As a result of providing an arrangement wherein the cannula 23 and stylet 22 are rotated relative to one another before sampling, the recess 24 can be arranged on the same side as the proximal leading edge 35 of the stylet 22. The longitudinal length of the recess 24 is preferably between 5 and 25 mm, more preferably between 10 and 20 mm.

According to the present invention, the length E, measured along a line parallel to the longitudinal axis of the stylet 22, between the distal end of the recess 24 and the proximal leading edge 35 of the stylet 22 is between 0 and 2.0 mm, more preferably 0 to 1.5 mm. Hence, the length C, i.e. the length between the distal end of the recess 24 and the extreme distal tip 26 of the solid stylet tip 25, can be considerably shortened in comparison to prior art assemblies (see length A in FIG. 1b). Thereby the minimum distance from a desired sample site to a non-penetrable or sensitive tissue is considerably shortened.

FIG. 3 also illustrates, as mentioned above, that the stylet 22 and cannula 23 have an oblique tip, and that the angle α between a longitudinal axis of the stylet 22 or cannula 23 and the leading edge of the oblique distal tip is essentially the same angle in the stylet 22 as in the cannula 23. This angle α can be within the range of 20 and 55 degrees, and is preferably between 25 and 35 degrees.

Figure 4:
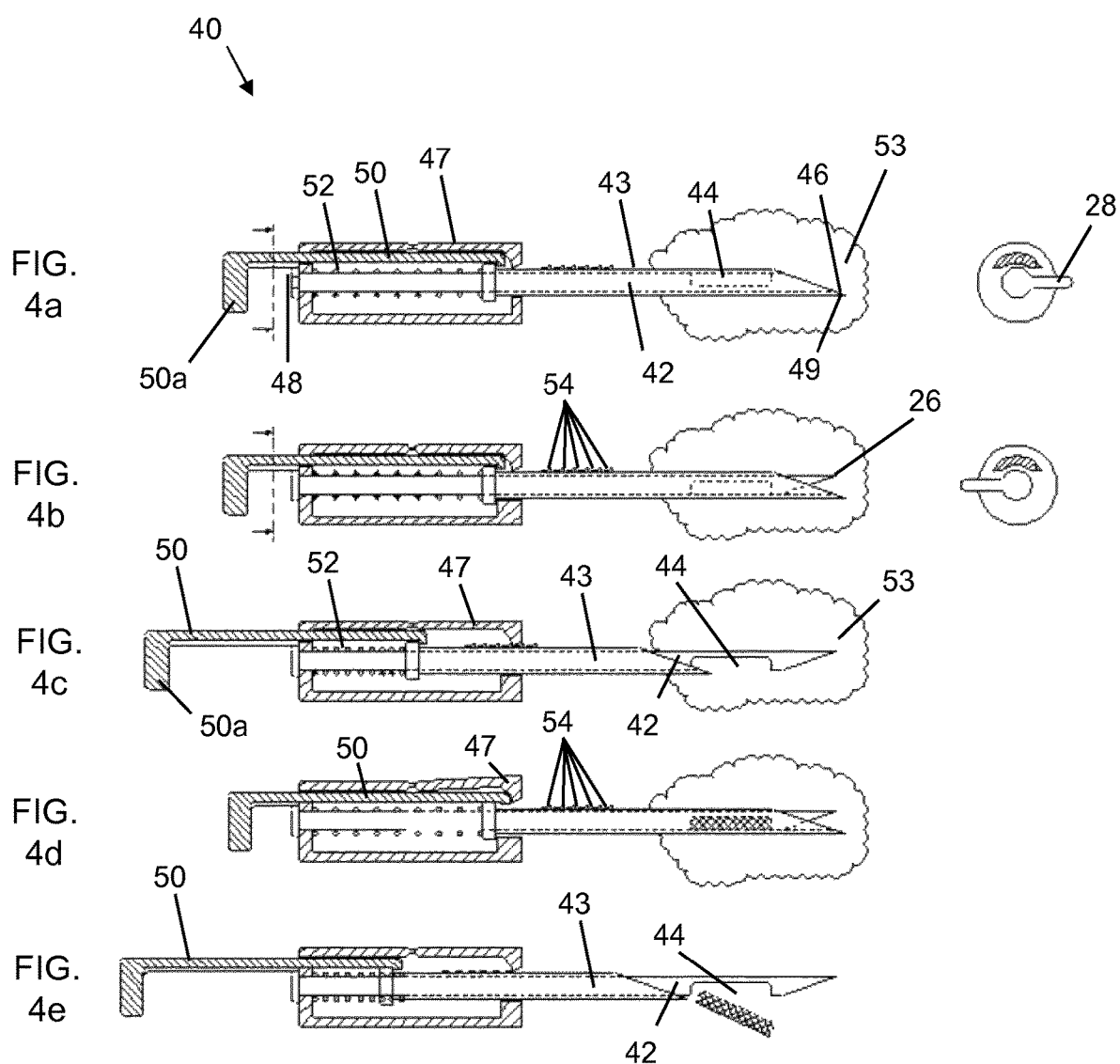
FIG. 4 illustrates a further embodiment of a biopsy assembly according to the present invention.

FIG. 4 shows another embodiment of a biopsy assembly according to the present invention. Similarly to FIG. 2, the figures in FIG. 4 are side views of a biopsy assembly 40 in different stages of operation, where the proximal end is on the left side and the distal end is on the right side of the figure. Referring to FIG. 4a, as in previous embodiments, a stylet 42 is arranged within a cannula 43 and is provided with a recess 44. Both the stylet 42 and the cannula 43 are provided with oblique tips, essentially slanted at equivalent angles, such that the leading edge of the assembly initially forms an essentially integrated slanted surface with a sharp tip, the tip comprising the stylet tip 46 in alignment with the cannula tip 49, as illustrated in FIG. 4a. The proximal ends of the stylet 42 and the cannula 43 are arranged within a housing 47 for guiding and manipulating the operation of the stylet 42 and the cannula 43.

In this embodiment, the stylet 42 protrudes from the distal end of the housing 47 and is arranged in the housing 47 such that it cannot move axially, but can rotate within the housing 47 and cannula 43. Furthermore, a rotating member 48 is fixedly attached to the proximal end of the stylet 42. A moving member 50 is at its distal end arranged to initially retain the cannula 43 by holding on to a proximal ledge of the cannula 43. A compression spring 52, enclosing the stylet 42, is mounted between an inner wall of the proximal end of the housing 47 and the proximal end of the cannula 43. The spring force acts on the cannula 43 in a distal direction, such that the stylet 42 and cannula 43 are kept in alignment. The proximal end of the moving member 50 protrudes out of the housing towards the user and comprises a handle 50*a*.

In use, the biopsy assembly 40 is inserted percutaneously into a patient's body, such that the distal end is placed inside a tissue mass 53 from which a sample is desired, as is shown in FIG. 4*a*. For simplicity, the skin and other tissue is not shown in the figures. As in the previous embodiments, the assembly can either be inserted on its own, through e.g. soft tissue, or, if a sample site is located behind or within a hard tissue, such as bone or cartilage, a drill arrangement can be used to create an access hole for the assembly.

The stylet 42 of the embodiment in FIG. 4 is provided with a recess 44 along one side of the solid stylet 42. The recess 44 is arranged on the same side as the proximal edge of the slanted tip as can be seen in the side views of FIG. 4.

In this embodiment a rotating member 48 is arranged in operative connection with the proximal end of the stylet 42, configured such that when the proximal end, e.g. a handle or knob, of the rotating member 48 is rotated, the stylet 42 will rotate within the cannula 43, such that the recess 44 is moved from one side to the other in relation to the cannula 43. This is illustrated in the difference between FIGS. 4*a* and 4*b*. The drawings on the far right show a proximal view of the biopsy assembly depicted in the respective left drawing. As can be seen when comparing the configuration of the assembly in FIG. 4*a* with that of FIG. 4*b*, when the handle of rotating member 48 is rotated approximately 180 degrees, the stylet 42 is rotated within the cannula 43.

In an alternative embodiment (not shown in the figures) a rotating member can be configured to rotate the cannula 43 instead, keeping the stylet 42 and housing 47 rotationally fixed in relation to each other. In a further embodiment, a torsion spring can be used as a rotating member to execute the rotation, as described for FIG. 2. Regardless of how the stylet or the cannula is rotated in relation to the rest of the assembly, i.e. whether it is done manually or by using a torsion spring, the end result regarding the orientation at the distal end of the stylet 42 and the cannula 43 in relation to each other is the same as illustrated in FIG. 4*b*, i.e. that the stylet 42 and cannula 43 are rotated 180 degrees in relation to each other, and the stylet tip 46 and the cannula tip 49 are on opposite sides of a longitudinal axis of the assembly.

After rotation of the stylet 42 and the cannula 43 in relation to each other, the moving member 50 is pulled back by the user, e.g. by pulling on the handle 50*a*. As the moving member 50 is arranged to retain the cannula 43 by holding on to a proximal ledge of the cannula 43, the cannula 43 will also be pulled back, as shown in FIG. 4*c*. However, the stylet 42 is prevented from moving axially within the housing 47. Hence, pulling back on the moving member 50 will expose the sample recess 44 to the desired tissue 53, and also compress the spring 52 between the housing wall and proximal end of the cannula 43. Furthermore, the cannula 23 is provided with multiple retaining protrusions 54 along the outside. These protrusions 54 are adapted such that when the cannula 43 is pulled in a proximal direction, as is shown in FIG. 4*c*, such that the protrusions are pulled into the housing 47, the housing wall will easily slide over them. However, the protrusions 54 prevent the cannula 43 from sliding back in a distal direction as a result of the spring force generated by the spring 52.

In an alternative embodiment, not shown in the figures, the proximal movement of the cannula can be executed by either a compression spring, arranged around the moving member 50 outside the housing, or a tension spring, arranged within the housing, to push or pull the moving member 50 and the cannula in a proximal direction.

After exposing the recess 44 to the sample tissue, the user pushes the moving member 50 in the distal direction, which will slide along the cannula 43. Alternatively, the distal movement of the moving member 50 could be executed by using springs, as previously described. The moving member 50, retaining protrusions 54 and housing 47 are configured such that when the distal end of the moving member 50 reaches the distal end of the housing 47, it will press away the housing wall 47 from the retaining protrusions 54, such that the cannula 43 is released from the retaining protrusions 54, and is rapidly pushed forward by the action of the spring 52, such that the leading edge of the cannula 43 severs the tissue and retains a tissue sample within the recess 44 and the cannula walls 43. This is illustrated in FIG. 4*d*.

As described in connection with the embodiments of FIG. 2, it is understood that different configurations of spring mechanisms can be used, using one or several compression and/or tension springs, as long as the resulting effect that is achieved is that the recess 44 of the stylet 42 is first exposed to the tissue mass 53, and thereafter the cannula 43 is moved forward to sever the tissue sample.

The embodiments using either semi-automatic or fully automatic sampling steps, as described above, can be combined with either manual or automatic rotation of the stylet 42 and cannula 43 in relation to each other, as described in relation to FIGS. 4*a* and 4*b* above.

After the sample is contained within the recess 44 and cannula walls, the biopsy assembly 40 is withdrawn from the sample site and the patient's body, e.g. by pulling on the housing 47 in a proximal direction. When the tissue sample is to be released from the biopsy assembly, the moving member 50 is pulled back again, such that the cannula 43 is pulled back and the tissue sample is exposed.

Even though the embodiment describing in relation to FIG. 4 differs in function from the embodiment described in FIG. 2, the embodiment of FIG. 4 also has the tip configuration shown in FIG. 3 and thereby the advantages described in relation to FIG. 3 apply also to this embodiment.

Figure 5:
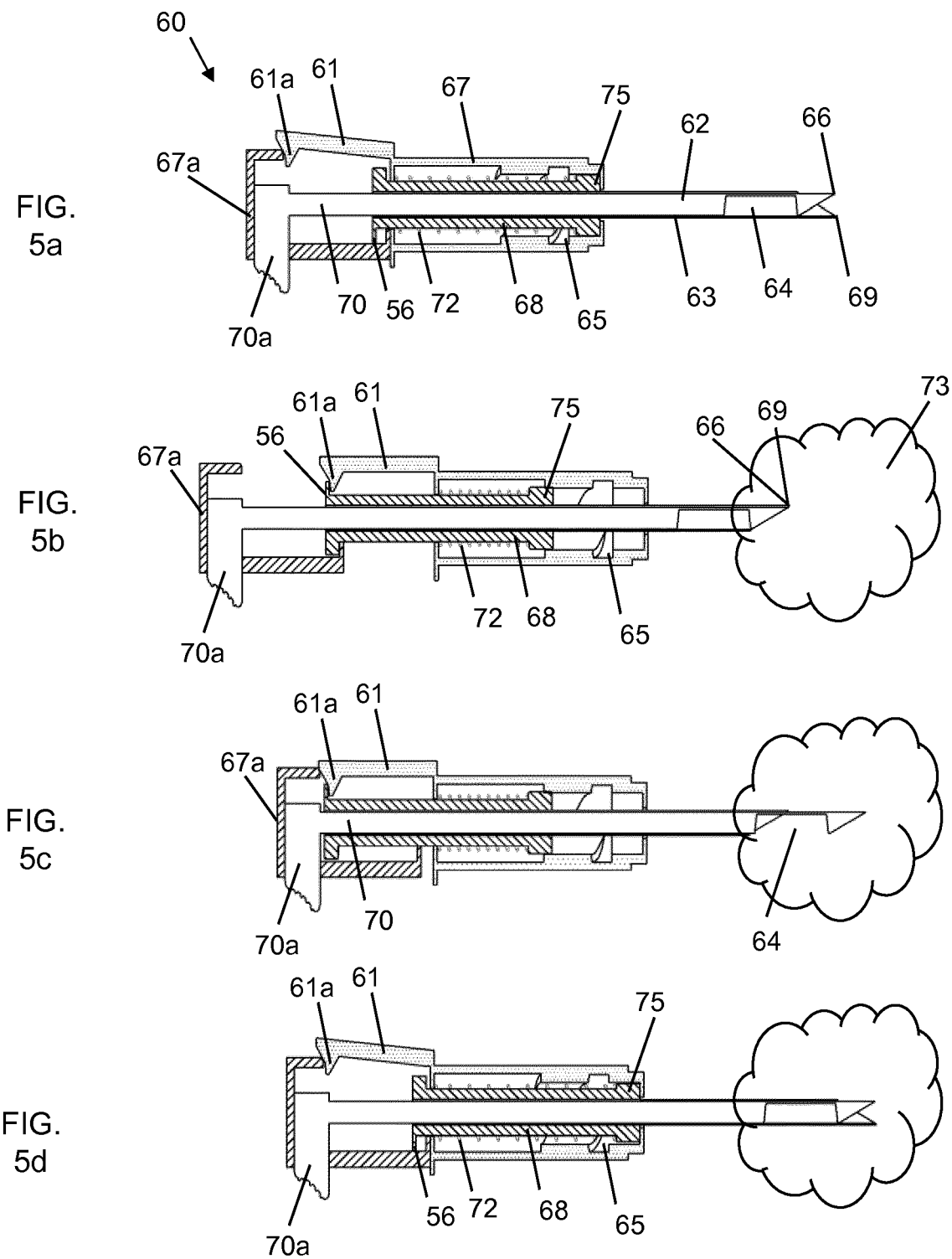
FIG. 5 illustrates yet another embodiment of a biopsy assembly according to the present invention.

FIG. 5 illustrates yet another embodiment of the present invention and its function. Similar to previous embodiments described, the FIGS. 5*a* to 5*d* are side views of an assembly in different stages of operation, where the proximal end is on the left side and the distal end is on the right side of the figure. As in previous embodiments, the biopsy device 60 is configured such that a sampling recess is arranged on the same side as and close to a proximal leading edge of a stylet with a slanted tip, and rotation of a cannula relative to the stylet is performed prior to tissue sampling. However, in the embodiment of FIG. 5, the rotational movement is coupled to axial movement of the cannula, and automatic, from a user's perspective.

A stylet or needle 62 is arranged within a cannula 63 and is provided with a recess 64 for containment of a tissue sample. Both the stylet 62 and the cannula 63 are provided with oblique tips, essentially slanted at equivalent angles. The recess 64 is arranged on the same side as the proximal edge of the slanted tip of the stylet 62. In this embodiment, the device is delivered to the user in the configuration shown in FIG. 5*a*, wherein the two oblique tips are arranged in opposite orientations, and the biopsy device 60 as a whole is arranged in a compact and relaxed state, suitable for packaging and transport. The distal tips 66, 69 of the stylet 62 and cannula 63 are longitudinally essentially in line with each other, but on opposite sides of the longitudinal axis of the biopsy device 60, as shown in FIG. 5*a*.

The proximal ends of the stylet 62 and the cannula 63 are arranged within a housing 67 for guiding and manipulating the operation of the stylet 62 and the cannula 63. In this embodiment, the stylet 62 is axially movable within the cannula 63 and the housing 67. The cannula 63 is arranged within and fixedly attached to an elongated essentially cylindrically shaped rotating member 68. The rotating member 68 is arranged in the housing 67 such that it can rotate within the housing 67. On an interior surface of the housing 67 is provided one or several helical grooves 65, adapted to interact with a distal rotational element 75 of the rotating member 68. As shown in FIG. 5, the distal rotational element 75 has a shape such that when the rotating member 68 is moved in a proximal direction, along the longitudinal axis, within the housing 67, the distal rotational element 75 will interact with the helical grooves 65, and cause rotation of the rotating member 68. Thus, as the rotating member 68 is fixedly attached to the cannula 63, a proximal movement of the rotating member 68 will cause the cannula 63 to rotate around the longitudinal axis of the device. Preferably, the helical grooves are adapted such that the cannula 63 is rotated by approximately 180 degrees when the rotating member 68 is fully pulled back in a proximal direction. This will cause the distal tip 69 of the cannula 63 to rotate approximately 180 degrees such that the distal oblique tips 66, 69 of the cannula 63 and the stylet 62 are aligned, as illustrated in FIG. 5b. It is to be noted that the cannula and stylet are now arranged in the configuration also illustrated in FIG. 3, which has been described above.

It is to be noted that other arrangements of a rotational member and the inside shape of a housing are within the scope of the present invention, as long as the configuration is adapted such that longitudinal movement of the rotational member automatically causes essentially simultaneous rotational movement of the rotational member. E.g. pins, on either the rotational member or the inside of the housing, and corresponding grooves can be used.

In the embodiment of FIG. 5, the stylet 62 is provided with a proximal elongated extension, forming a moving member 70, with a proximal handle 70a. A proximal part 67a of the housing is axially movable in relation to the distal part of the housing 67. The proximal handle 70a is arranged in a longitudinal slit of the proximal part 67a of the housing and partially protruding out of one side of the housing 67a (as can be understood by FIG. 5). The function of the protruding part, forming a knob or button, will be described in connection to FIG. 6. The proximal end of handle 70a is arranged adjacent to a proximal end wall of the proximal housing 67a.

The biopsy device 60 is further provided with a fastening member 61, which is fixedly attached at its distal end to the distal part of the housing 67 and wherein the proximal end is arranged to strive inwards and comprises a radially or centrally directed catch or hook 61a. The fastening member 61 is thus arranged such that when the proximal part 67a of the housing, and thus the proximal handle 70a, is pulled in a proximal direction, the fastening member 61 will slide along the device until it reaches a protruding flange 56 at the proximal end of rotating member 68, where it will snap into a locked position, holding the rotating member 68 in its most proximal position relative to the distal housing 67, as can be understood when comparing FIGS. 5a and 5b.

A compression spring 72 is mounted such that it encloses the rotating member 68 and is arranged between a central inner wall of the housing 47 and the distal rotational element 75, as can be seen in FIG. 5a. The spring force of compression spring 72 acts on the rotating member 68 in a distal direction. Thus, the extended configuration of FIG. 5b is maintained by the interaction of protruding flange 56 and the fastening element 61, and the spring force exerted by the spring 72. The shape of the protruding flange 56 can be any suitable circumferential ring shape, such as a continuous ring shape with a notch or indentation allowing accommodation of a radially or centrally directed catch or hook 61a on a fastening member 61.

Thus, to load the biopsy device for a biopsy procedure, a user may pull back on the proximal part 67a of the housing and the handle 70a at the proximal end of the device 60 and/or pull on the distal housing in a distal direction. This will cause rotating member 68 to be pulled back inside the proximal housing 67a. As the rotating member 68 is pulled back it will automatically rotate, due to the interaction of distal rotational element 75 with the helical grooves 65. Thus, in this embodiment, no manual rotation by the user needs to be performed, and the resulting rotation of the cannula 63 relative to the stylet 62 is smoothly and precisely performed, as well as automatically executed, when pulling on both ends of the device.

In addition, when the proximal part 67a of the housing is pulled away from the distal end of the housing 67, the compression spring 72 will be compressed. At the end position of extension, the fastening device 61, which is fixedly attached to the distal part of the housing 67, will hold the rotating member 68 in a proximal position.

It is to be noted that when the device is extended before use, as described above, the stylet 62 and cannula 63 are pulled back an equal distance, i.e. the distal tips 66, 69 are maintained in an fixed longitudinal position relative to each other throughout the extension step, as shown in FIGS. 5a and 5b, while the tips are rotated from opposite positions to being in alignment with each other. Thus, after extension of the device, the leading edge of the assembly forms an essentially integrated slanted surface with a sharp tip.

In the configuration of FIG. 5b, the device is ready for penetration of tissue. As described for previous embodiments, the biopsy assembly 60 is inserted percutaneously into a patient's body, such that the distal end is placed adjacent or slightly inserted into a tissue mass 73 from which a sample is desired. For simplicity, the skin and other tissue is not shown in the figures. In one embodiment the assembly can be inserted on its own, through e.g. soft tissue. In another embodiment, if a sample site is located behind or within a hard tissue, such as bone or cartilage, a drill arrangement can be used to create an access hole for the assembly, as described for previous embodiments.

To initiate the sampling procedure, a user presses on the proximal part 67a of the housing, and thus on the handle 70a, in a distal direction. As the handle 70a is coupled to the stylet 62 via the moving member 70, the stylet 62 will be moved in a proximal direction. This results in the configuration of FIG. 5c, where the distal tip of the stylet 62 protrudes out of the cannula 63, and the sampling recess 64 is exposed to the target tissue 73. Target tissue will enter the sample recess 64.

The user may then continue to press on the proximal moving member 70a, via the distal housing 67a, in a distal direction. Due to the slanted shape of the hook 61a on fastening member 61, as the user continues to press on the proximal part 67a of the housing, and thus on the handle 70a, in a distal direction, the hook 61a will be pressed outwards, and release the protruding flange 56 on the rotating member. Due to the spring force of spring 72, the rotating member 68, and thus also the cannula 73, will be rapidly pushed forward. This will automatically cause two sequential events. First, as the distal rotational element 75 is pushed forward, it will interact again with the helical grooves 65, and thereby cause rotation of the rotating member 68 and hence also the cannula, by preferably approximately 180 degrees. Secondly, due to continued forward movement of the cannula 63, directly after rotation, the leading edge of the cannula 43 will pass over the sample recess 64, and thus sever the tissue. The cannula will retain a tissue sample within the recess 64 and the cannula walls 63. This is illustrated in FIG. 5*d*.

One advantage of the embodiment described in FIGS. 5*a* to 5*d* is that a small number of manipulation by a user, results in several sequential steps. First, a user pulls on both ends of the biopsy device, which causes loading (compression) of the spring as well as rotation of the cannula relative to the stylet. Second, after placing the device close to or inside a target tissue, pressing on the proximal end will first cause the stylet to project into the tissue, allowing target tissue to enter the sample recess, and continued pressing on the proximal end will first cause rotation of the cannula relative to the stylet, and thereafter severing and capture the tissue sample. Thereby the entire sampling procedure is easier and smoothly executed by a user.

As described in connection with the previous embodiments, it is understood that different configurations of spring mechanisms, catches and rotational members can be used, resulting in semi-automatic or fully automatic sampling steps, as long as the resulting effect is that the recess 64 of the stylet 62 is first exposed to the tissue mass 73, and thereafter the cannula 63 is moved forward to sever the tissue sample, and that rotation of the stylet 62 and cannula 63 in relation to each other takes place prior to the sampling.

After the sample is safely contained within the recess 64 and cannula walls, the biopsy assembly 60 is withdrawn from the sample site and the patient's body, e.g. by pulling on the housing 67 in a proximal direction.

Even though the embodiment describing in relation to FIG. 5 differs in function from the embodiment described in FIGS. 2 and 4, the embodiment of FIG. 5 also has the tip configuration shown in FIG. 3. Consequently, the advantages described in relation to FIG. 3 apply also to the embodiment of FIG. 5. Due to the device being able to rotate the cannula and stylet in relation to each other prior to tissue sampling, it is possible to provide a device with a sample recess very close to the tip of the device, and hence samples can be obtained at a close distance to tissue which is impenetrable or not suitable to penetrate for varying reasons. As described above, the inventive configuration allows the recess 64 can be arranged on the same side as the proximal leading edge of the stylet 62, without compromising integrity or risking contamination of the sample. The length E (see FIG. 3), measured along a line parallel to the longitudinal axis of the stylet, between the distal end of the recess and the proximal leading edge of the stylet can be kept short without risking leakage.

Figure 6:
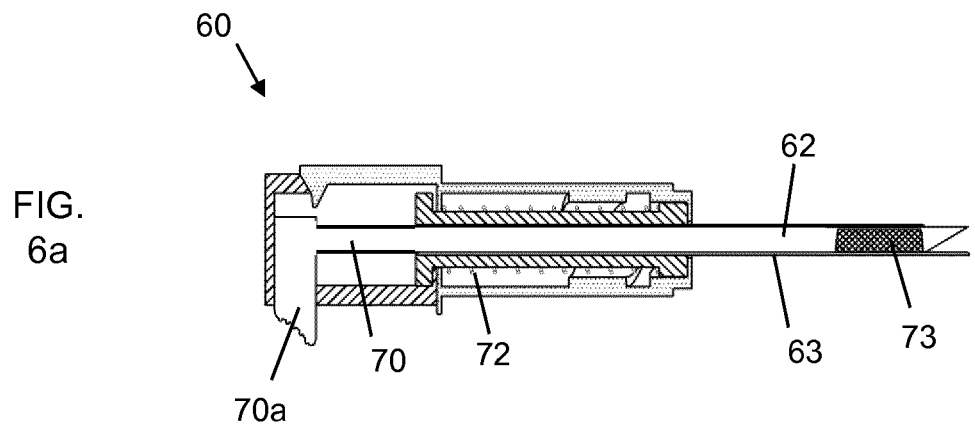
FIG. 6 illustrates a further embodiment of a biopsy assembly according to the present invention.
Figure 6:
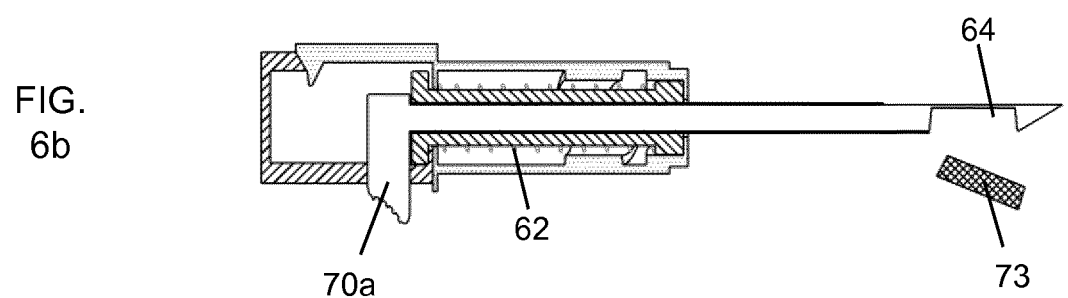

FIG. 6 illustrates yet another embodiment of the present invention, similar to the biopsy device of FIG. 5. Similar to previous embodiments, FIG. 6 shows a side view of a biopsy device in cross-section, the left side of the figure being the proximal end, closest to a user, and the right side being a distal end, closest to a sample site, when used in tissue sampling. FIG. 6 shows how a tissue sample may safely and securely be released after sampling, while minimizing the risk of damage to an obtained tissue sample. After obtaining a tissue sample, for example as described in FIG. 5, the biopsy device 60 is withdrawn from the patient, and the tissue sample needs to be released from the device for analysis. Normally, a tissue sample is collected in a container, on a microscopic slide, and/or in e.g. a saline solution for preservation and analysis. In the biopsy device 60 shown in FIG. 6, while holding the distal end of the device where a sample is to be released, a user moves the knob or button 70*a* in a distal direction, thereby moving the stylet 62 distally to release the tissue sample from within the cannula 63. This is illustrated by comparing FIGS. 6*a* and 6*b*.

This release procedure eliminates tensioning and/or releasing a spring, and thus minimizes the risk of accidentally having the stylet 82 move uncontrollably forward and/or spring back if the button 70*a* is released prematurely by the user. In addition, the user can also control manually how fast the sample is to be released, e.g. if the tissue type sampled is particularly sensitive for some reason, the user can release the sample very slowly and carefully.

The present invention also relates to the method of use of a biopsy assembly as described above. In summary, the method comprises the steps of:
  inserting, into or adjacent a desired sample site, the outer cannula (23, 43, 63) provided with the stylet (22, 42, 62), and
  rotating the stylet (22, 42, 62) or the cannula (23, 43, 63) around a common axis, such that the cannula (23, 43, 63) and the stylet (22, 42, 62) are rotated relative to one another, and
  moving the stylet (22, 42, 62) and the cannula (23, 43, 63) axially relative to each other such that the recess (24, 44, 64) is exposed to the tissue which is thereby pressed into said recess, and
  moving the stylet (22, 42, 62) and the cannula (23, 43, 63) axially relative to each other such that a distal edge of the distal tip of the cannula (23, 43, 63) severs the tissue and the biopsy assembly retains the tissue sample within the recess (24, 44, 64) and the cannula (23, 43, 63).

In a preferred embodiment, the method comprises further that the distal tips of the stylet (22, 42, 62) and the cannula (23, 43, 63) are aligned and oriented during insertion such that an essentially flat leading surface is formed at the distal tip of the biopsy assembly. Furthermore, the distal tips of the stylet (22, 42, 62) and the cannula (23, 43, 63) are preferably essentially aligned longitudinally after the rotation step but prior to the moving steps.

In another preferred embodiment, the method step of rotation of the cannula and/or stylet relative to each other is coupled to the step of moving the cannula or stylet axially, such that axial movement causes rotational movement. In another embodiment, the method comprises two or more steps of rotational movement of the cannula and/or stylet. Preferably, these rotational steps are directly coupled to axial movement of the cannula and/or stylet.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A biopsy assembly for obtaining a tissue sample, comprising
  an outer tubular cannula provided with an oblique distal tip,
  a stylet configured to be disposed axially within said cannula and being provided with an oblique distal tip, the stylet having a recess arranged along a side of said stylet, and the recess being configured to receive said tissue sample, a housing configured to guide and to manipulate said cannula and stylet, the housing including, on an interior surface thereof, one or more helical grooves, and the stylet being axially movable within the cannula and the housing, a rotating member mounted at a proximal end of said stylet or said cannula, the rotating member being configured to rotate said stylet or said cannula around a common axis such that said cannula and said stylet are rotated relative to one another, wherein the rotating member is configured to rotate said stylet and said cannula relative to one another prior to tissue sampling such that a most distal edge of said oblique distal tip of said cannula is arranged at the same side as said recess when the tissue sampling is performed, and wherein a length, measured along a line parallel to a longitudinal axis of said stylet from a distal end of said recess and to a proximal leading edge of said stylet is greater than 0 mm and less than or equal to 2.0 mm, the rotating member comprising a distal rotational element configured such that when the rotating member is moved in a proximal direction along the longitudinal axis within the housing, the distal rotational element interacts with the one or more helical grooves so as to cause rotation of the rotating member, and the rotating member being elongated and substantially cylindrical, and arranged in the housing so as to be rotatable within the housing, and the cannula being arranged within and fixedly attached to the rotating member, at least one spring configured to exert a spring force on said cannula in an axial direction to move said cannula axially and to rapidly move said cannula distally to sever said tissue sample, and a release mechanism configured to release said cannula for axial movement relative to said stylet after receiving said tissue sample, the release mechanism comprising at least one retaining protrusion configured to inhibit distal movement of said cannula until said release mechanism is activated, wherein a proximal part of said housing is configured to be axially movable in relation to a distal part of said housing, and said stylet is provided with a proximal elongated extension forming a moving member with a proximal handle, the proximal handle arranged in a longitudinal slit of said proximal part of said housing and partially protruding out of one side of said housing.

2. The biopsy assembly according to claim 1, wherein said recess is provided on a same side of said stylet as a proximal leading edge of said oblique distal tip of said stylet.

3. The biopsy assembly according to claim 1, wherein an angle ($\alpha$) between a longitudinal axis of said stylet and a leading edge of said oblique distal tip of said stylet is within a range of 20 to 55 degrees.

4. The biopsy assembly according to claim 1, further comprising at least one moving member for moving said cannula in an axial direction.

5. The biopsy assembly according to claim 1, further comprising at least one moving member configured to move said stylet in an axial direction.

6. The biopsy assembly according to claim 1, wherein said rotating member is arranged within said housing such that axial movement of said rotating member causes rotation of said cannula relative to said stylet.

7. The biopsy assembly according to claim 1, wherein the one or more helical grooves are structured such that the cannula is rotated by approximately 180 degrees when the rotating member is fully pulled back in the proximal direction.

8. The biopsy assembly according to claim 7, wherein the oblique distal tip of the cannula and the oblique distal tip of the stylus are aligned when the cannula is rotated by approximately 180 degrees.

\* \* \* \* \*